(12) United States Patent
Mohr et al.

(10) Patent No.: US 7,785,355 B2
(45) Date of Patent: Aug. 31, 2010

(54) SYSTEM FOR RIB FIXATION

(75) Inventors: Marcus Mohr, Portland, OR (US);
Michael Bottlang, Portland, OR (US);
James C. Krieg, Portland, OR (US);
William B. Long, Portland, OR (US);
Steven M. Madey, Lake Oswego, OR (US)

(73) Assignee: Synthes USA, LLC, West Chester, PA (US)

( * ) Notice: Subject to any disclaimer, the term of this patent is extended or adjusted under 35 U.S.C. 154(b) by 595 days.

(21) Appl. No.: 10/971,531

(22) Filed: Oct. 20, 2004

(65) Prior Publication Data

US 2006/0085000 A1  Apr. 20, 2006

(51) Int. Cl.
*A61B 17/80* (2006.01)
(52) U.S. Cl. .................... 606/280; 606/283
(58) Field of Classification Search .......... 606/69–71
See application file for complete search history.

(56) References Cited

U.S. PATENT DOCUMENTS

| | | | |
|---|---|---|---|
| 3,593,709 A | 7/1971 | Halloran | |
| 3,900,025 A | 8/1975 | Barnes, Jr. | |
| 4,201,215 A | 5/1980 | Crossett et al. | |
| 4,966,599 A * | 10/1990 | Pollock | 606/69 |
| 5,443,516 A | 8/1995 | Albrektsson et al. | |
| 5,487,741 A | 1/1996 | Maruyama et al. | |
| 5,741,259 A | 4/1998 | Chan | |
| 5,931,839 A | 8/1999 | Medoff | |
| 6,077,271 A * | 6/2000 | Huebner et al. | 606/101 |
| 6,117,160 A | 9/2000 | Bonutti | |
| 6,139,548 A | 10/2000 | Errico | |
| 6,228,087 B1 | 5/2001 | Fenaroli et al. | |
| 6,302,884 B1 | 10/2001 | Wellisz et al. | |
| 2004/0260291 A1 * | 12/2004 | Jensen | 606/69 |
| 2005/0085819 A1 * | 4/2005 | Ellis et al. | 606/71 |
| 2005/0192578 A1 * | 9/2005 | Horst | 606/69 |
| 2005/0234458 A1 * | 10/2005 | Huebner | 606/69 |
| 2005/0273104 A1 * | 12/2005 | Oepen et al. | 606/69 |

FOREIGN PATENT DOCUMENTS

| | | |
|---|---|---|
| DE | 2515430 | 11/1975 |
| SU | 610518 | 5/1978 |
| SU | 718097 | 2/1980 |
| SU | 862937 | 9/1981 |
| SU | 897233 | 1/1982 |
| SU | 1049054 | 10/1983 |
| SU | 1223901 | 4/1986 |
| SU | 1644932 | 4/1991 |

OTHER PUBLICATIONS

*Operative stabilization of nonpenetrating chest injuries*, Bryan P. Moore et al., pp. 619-630, 1975.
*Surgical stabilization of traumatic flail chest*, F. Tarazona et al., pp. 521-527, 1975.

(Continued)

*Primary Examiner*—Thomas C Barrett
*Assistant Examiner*—Nicholas Woodall
(74) *Attorney, Agent, or Firm*—Woodcock Washburn LLP

(57) ABSTRACT

System, including methods, apparatus, and kits, for fixing ribs with bone plates.

28 Claims, 6 Drawing Sheets

OTHER PUBLICATIONS

Operative stabilization for flail chest after blunt trauma, Arthur N. Thomas et al., *The Journal of Thoracic and Cardiovascular Surgery*, vol. 75, No. 6, pp. 793-801, Jun. 1978.

Chest Wall Injuries, Trunkey DD, *Cerviothoracic Trauma*, vol. 3. pp. 129-149, 1986.

*Rib Fracture Healing after Osteosynthesis with Wire Mesh Titanium and Screws: A Histological Study in Sheep*, Klein et al., pp. 347-354, 1989.

Open Fixation of Flail Chest After Blunt Trauma, George B. Haasler, MD, *The Society of Thoracic Surgeons*, pp. 993-995, 1990.

Strut Fixation of an Extensive Flail Chest, Rodney J. Laudreneau, MD et al., *The Society of Thoracic Surgeons*, pp. 473-475, 1991.

Operative Chest Wall Stabilization in Flail Chest—Outcomes of Patients With or Without Pulmonary Contusion,Gregor Voggenreiter, MD et al., *American College of Surgeons*, pp. 130-138, 1998.

Use of 3.5mm Acetabular Reconstruction Plates for Interal Fixation of Flail Chest Injuries, J. Rodrigo Oyarzun et al., *Section of Cardiothoracic Surgery*, pp. 1471-1474, 1998.

Bioabsorable Poly-L-Lactide Costal Coaptation Pins and Their Clinical Application in Thoroacotomy, Akitoshi Tatsumi et al., *Original Articles: General Thoracic*. pp. 765-768, 1999.

Painful Nonunion of Multiple Rib Fractures Managed by Operative Stabilization, Robert Cacchione, MD et al., *The Journal of Trauma, Injury, Infection and Critical Care*, vol. 48, No. 2, pp. 319-321, 2000.

Internal Fixation in Osteoporotic Bone, An, Y.H., pp. 83, 2002.

Absorable Plates for Rib Fracture Repair: Preliminary Experience, John C. Mayberry, *Journal of Trauma Injury, Infection and Critical Care*, vol. 55, No. 5, pp. 835-839, Nov. 2003.

*Clinically Oriented Anatomy*, Keith Moore et al., Fourth Edition, pp. 70-71, 2004.

Operative Chest Wall Fixation with Osteosynthesis Plates, Christine Engel et al., *The Journal of Trauma, Injury, Infection and Critical Care*, vol. 58, No. 1, pp. 181-186, 2005.

*Biomechanics Laboratory*, Legacy Biomechanics Laboratory, available at www.biomechresearch.org/sling.html, Jan. 2006.

*Resorable Plate* from Osteomed, available at www.osteomedcorp.com/images/library/resorbfixation.gif, Feb. 2006.

*Rib Plate*, from Sanatmetal Catalog, available at www.sanatmetal.hu/catalog/pict/1_5_89a_1.jpg, Feb. 2006.

Lardinois D., Krueger T., Dusmet M., Ghisleta N., Gugger M., Ris H., Pulmonary Function Testing After Operative Stabilisation of the Chest Wall for Flail Chest *European Journal of Cardio-thoracic Surgery* (2001) vol. 20:496-501.

Ng A., Giannoudis P., Bismil Q., Hinsche A., Smith R., Operative Stabilisation of Painful Non-united Multiple Rib Fractures. *Injury* (2001) vol. 32:637-639.

Slater M., MayberryJ., Trunkey D., Operative Stabilization of Flail Chest Six Years after Injury. *The Annals of Thoracic Surgery* Aug. 2001:600-601.

Tanaka H., Yukioka T., Yamaguti Y., Shimizu S., Goto H., Matsuda H., Shimazaki S., Surgical Stabilization or Internal Pneumatic Stabilization? A Prospective Randomized Study of Management of Severe Flail Chest Patients. *Journal of Trauma* (2002) vol. 52:727-732.

Current Clinical Techniques, Section II, date unknown, pp. 81 & 82.

\* cited by examiner

SYSTEM FOR RIB FIXATION

CROSS-REFERENCE TO PRIORITY APPLICATION

This application is based upon and claims the benefit under 35 U.S.C. §119(e) of the following U.S. provisional patent application, which is incorporated herein by reference in its entirety for all purposes: Ser. No. 60/612,677, filed Sep. 24, 2004, titled "System for Rib Fixation," and naming Markus Mohr, Michael Bottlang, James C. Krieg, William B. Long, and Steven M. Madey as inventors.

CROSS-REFERENCES TO RELATED PUBLICATIONS

This application incorporates herein by reference the following publications:
1. Cacchione R, Richardson J, Seligson D. Painful Nonunion of Multiple Rib Fractures Managed by Operative Stabilization. *J. Trauma.* (2000). 48:319-21.
2. Lardinois D, Krueger T, Dusmet M, Ghisleta N, Gugger M, Ris H. Pulmonary Function Testing after Operative Stabilisation of the Chest Wall for Flail Chest. *Eur. J. Cardiothorac. Surg.* (2001). 20:496-501.
3. Ng A, Giannoudis P, Bismil Q, Hinsche A, Smith R. Operative Stabilisation of Painful Non-united Multiple Rib Fractures. *Injury.* (2001). 32:637-639.
4. Slater M, Mayberry J, Trunkey D. Operative Stabilization of Flail Chest Six Years after Injury. *Ann Thorac Surg.* (2001). August 2001 600-601.
5. Tanaka H, Yukioka T, Yamaguti Y, Shimizu S, Goto H, Matsuda H, Shimazaki S. Surgical Stabilization or Internal Pneumatic Stabilization? A Prospective Randomized Study of Management of Severe Flail Chest Patients. *J. Trauma.* (2002). 52:727-732.

BACKGROUND

Chest wall fractures, and in particular, fractures of rib bones of the rib cage, can cause potentially life-threatening respiratory insufficiencies, accounting for up to 50% of the mortality in thorax injuries. Fracture of a rib bone can occur at any location along the bone. However, the most critical fractures often involve multiple fracture of each of a set of adjacent rib bones. In particular, if four or more consecutive rib bones of the rib cage each sustain two or more fractures, for example, to create a column of bone fragments flanked by fractures sites, the fracture pattern is referred to as a flail chest injury. In flail chest injury, a fractured region of the chest wall is detached from the remainder of the chest wall, that is, no longer held in position by the rib cage. Accordingly, this fractured region can move independently of the chest wall during respiration, resulting, for example, in lung collapse.

Flail chest injury may be treated non-operatively or operatively to restore the anatomy and physiological function of the chest wall. Non-operative treatment generally involves aggressive pain control and mechanical ventilation. As a result, non-operative treatment has been associated with prolonged stays in the hospital and increased mortality rates. Operative treatment generally involves reducing and stabilizing rib fractures with internal fixation devices (osteosynthesis hardware), such as wires and/or bone plates. Bone plates are sturdy devices that are installed on the surface of bones, for example, by securing the bone plates to bone with bone screws. The bone plates generally are positioned to span fractures or other discontinuities in the bones and thus keep bone fragments aligned and stabilized during healing. In treatment of flail chest injuries, bone plates may be secured to multiply fractured ribs, to effectively re-unify the rib cage as the ribs heal.

Operative stabilization of flail chest injuries, such as with bone plates, can provide significant benefits over non-operative treatment. For example, operative stabilization can reduce the need for, and thus the mortality associated with, prolonged mechanical ventilation. In addition, operative stabilization can dramatically reduce pain during respiration, yield faster fracture healing, prevent persistent respiratory compromise, and reduce costs for treatment.

Despite the widely accepted benefits of operative stabilization to treat flail chest injury, it is difficult to provide bone plates configured specifically for installation on rib bones, due to the complex and varying surface geometry of the rib cage. Accordingly, generic bone plates have been used to fix rib bones. These generic plates, as provided, are straight and generally planar. These generic plates thus require substantial bending, generally intra-operatively by a surgeon, to custom-contour each plate according to a target surface region of a particular rib bone. This substantial intra-operative bending may be undesirable for many reasons. For example, this bending generally increases the time a patient spends in surgery, increasing the cost of surgery and the risk of surgical or post-surgical complications (such as infection). In addition, substantial bending may weaken the bone plate. Furthermore, if a generic bone plate is not conformed sufficiently to the rib surface, the bone plate may apply a concentrated stress to the rib bone, which may fracture the rib bone.

SUMMARY

The present teachings provide a system, including methods, apparatus, and kits, for fixing ribs with bone plates.

DETAILED DESCRIPTION

The present teachings provide a system, including methods, apparatus, and kits, for fixing ribs with bone plates. The bone plates may be fabricated to have a pre-operative contour that is based on a surface geometry of human ribs. In particular, despite the seemingly complex geometry of ribs, the present teachings identify similar geometrical features of different ribs and/or of distinct surface regions disposed along a rib, allowing bone plates to be precontoured according to an averaged surface geometry of one or more ribs. The bone plates may be precontoured to include a longitudinal twist, an out-of-plane longitudinal curvature, and/or an in-plane longitudinal curvature, so that the bone plates, as supplied, conform more closely to rib surfaces than generic bone plates. Since the bone plates reflect an averaged shape of human ribs, these plates can be adjusted with minimal time and effort to reliably match the ribs of each individual patient.

Figure 1:
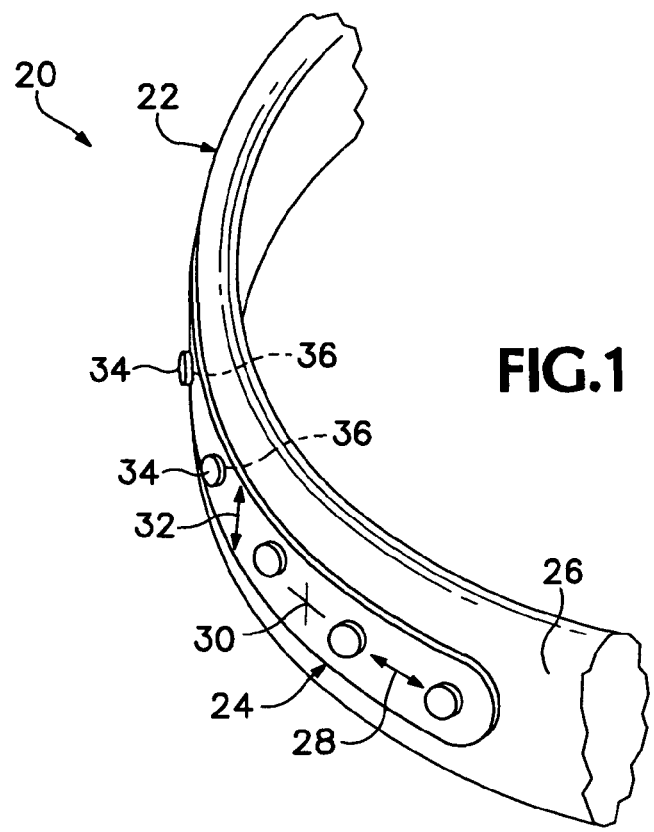
FIG. 1 is a view of an exemplary system for fixing a fractured rib bone with a precontoured bone plate, in accordance with aspects of the present teachings.

FIG. 1 shows an exemplary system 20 for fixing a fractured rib bone 22 with a bone plate 24. The bone plate may be precontoured for installation on rib bone 22 (and, optionally, one or more alternative rib bones), so that the bone plate substantially matches a region (or each of a plurality of regions) of the surface of the bone, generally a region included in outer surface 26. The outer surface may twist and/or bend as it extends along the rib, and thus the bone plate may twist and/or bend accordingly. In particular, twisting of the plate may include twisting generally about a longitudinal axis 28 of the bone plate. Bending of the bone plate may include in-plane longitudinal bending about a normal axis 30 of the bone plate, to provide in-plane curvature, and/or out-of plane longitudinal bending away from the long axis of the bone plate, about a bending axis generally parallel to transverse axis 32, to provide out-of plane longitudinal curvature. The bone plate may be secured to the rib bone, using, for example, bone screws 34 received in holes 36 of the bone plate. The bone plate may be secured as supplied, or the shape of the bone plate may be adjusted peri-operatively to improve the fit of the bone plate onto bone, generally before the bone plate is secured to bone.

The present teachings offer kits for fixing rib bones, and methods of using the kits. The kits may include at least two bone plates precontoured for installation on different rib bones. In some examples, at least one of the bone plates may be precontoured for use on at least two rib bones. Accordingly, the kit may have a smaller set of bone plates precontoured for use on a larger set of rib bones, to simplify manufacture of the kit and its use by a surgeon. Furthermore, each bone plate may be configured to be installed at any one of a plurality of positions along a rib bone. The kits may be used by selecting a bone plate for installation on a rib bone, based on the position of the rib bone (and/or a position of a target surface region within the rib bone). For example, if the left third rib of a patient is being fixed, a plate precontoured for use on the left third rib (and optionally other ribs) may be selected. The selected plate may include a plurality of holes, and may be secured to the rib bone by placing fasteners (such as bone screws) through the holes and into bone.

The system of the present teachings may offer substantial advantages over fixation with generic bone plates. For example, the system may provide rib plates that can be installed more easily and rapidly than generic bone plates. In particular, the system may eliminate substantially the time-consuming and difficult task of empirically contouring a generic plate from a linear, planar configuration. As a result, operation time, soft tissue exposure, and thus the risk of infection may be reduced during surgery. Furthermore, the system may allow surgeons with less experience in chest wall fixation to achieve high congruency between plates and ribs, thus reducing peak stresses at screw-bone interfaces that may be produced by nonconformity between plates and rib surfaces. Overall, the system of the present teachings may offer life-saving approaches for surgical treatment of severe chest wall injuries.

Further aspects of the present teachings are described in the following sections, including (I) precontoured rib plates and averaged surface geometries of ribs, (II) exemplary rib analysis and selection of pre-operative plate contours, (III) kits for fixing rib bones, (IV) methods of making precontoured rib plates, (V) methods of using precontoured rib plates, (VI) an exemplary rib plate, (VII) aspects of precontoured rib plates, and (VIII) selected embodiments.

I. Precontoured Rib Plates and Averaged Surface Geometries of Ribs

The present teachings provide precontoured bone plates (rib plates) for fixing rib bones. A precontoured rib plate, as used herein, is a rib plate shaped pre-operatively, that is, preshaped at any time before surgery is performed to install the plate. A rib plate thus may be precontoured during its manufacture (fabrication), that is, at any time before it is supplied to practitioners (such as surgeons), and/or may be precontoured, at least partially, by practitioners or technicians, among others, after the plate's fabrication but before surgery begins. A precontoured rib plate is preshaped to fit, at least approximately, on one or more surface regions of a rib bone(s). However, the shape of a precontoured rib plate also may be adjusted intra-operatively, that is, during surgery, for example, to improve the fit of the rib plate on bone at the site of installation. Further aspects of plate installation and shape adjustment are included in Section V.

A precontoured rib plate may be fabricated to include at least one pre-operative contour. A pre-operative contour, as used herein with reference to a rib plate, is any bend/twist in the rib plate that is created pre-operatively (but not necessarily by the act of bending/twisting). Pre-operative contours thus may include one or more longitudinal bends in the rib plate, in any suitable direction(s) away from linear, at any suitable position(s) along the rib plate, and with any suitable curvature(s). Alternatively, or in addition, pre-operative contours may include a twist in the rib plate, that is, a bend generally about the long axis of the bone plate. Aspects of creating pre-operative contours in rib plates during their fabrication are included below in Section IV.

Each pre-operative contour of a rib plate may be selected according to an averaged surface geometry of human ribs, so that the pre-operative contour substantially matches the averaged surface geometry. An averaged surface geometry, as used herein with reference to ribs, is a measure of the surface shape of the rib cage, averaged over any suitable number of surface regions within a rib bone, any suitable number of different ribs in the rib cage, and/or any suitable number of ribs from different individuals. The averaged surface geometry thus may represent a population-averaged geometry that is also inter-rib averaged and/or intra-rib averaged for a region of the rib cage. Any number of members from any suitable population may be used to provide a population-averaged surface geometry. Exemplary populations include adults, children, males, females, an ethnic group, and/or people of a selected range of sizes (e.g., size of rib cage, chest, frame, body, etc.), among others.

The averaged surface geometry may correspond to any suitable surface regions of ribs. The surface regions may be included in outer surfaces, inner surfaces, superior surfaces, and/or inferior surfaces, among others, of ribs. Outer surfaces, as used herein in reference to rib bones, include rib surfaces that face generally away from the long axis of the body. Outer surfaces thus may include anterior, posterior, medial, and/or lateral surface regions of the ribs. In some examples, outer surfaces may be preferred, because of the accessibility and width of these rib surfaces.

II. Exemplary Rib Analysis and Selection of Pre-operative Plate Contours

This section describes an exemplary approach for selecting pre-operative contours of rib plates based on an exemplary analysis of the surface geometry of human ribs. In this exemplary approach, the analysis of averaged surface geometry was performed on rib specimens from human cadavers, as described below.

Figure 2:
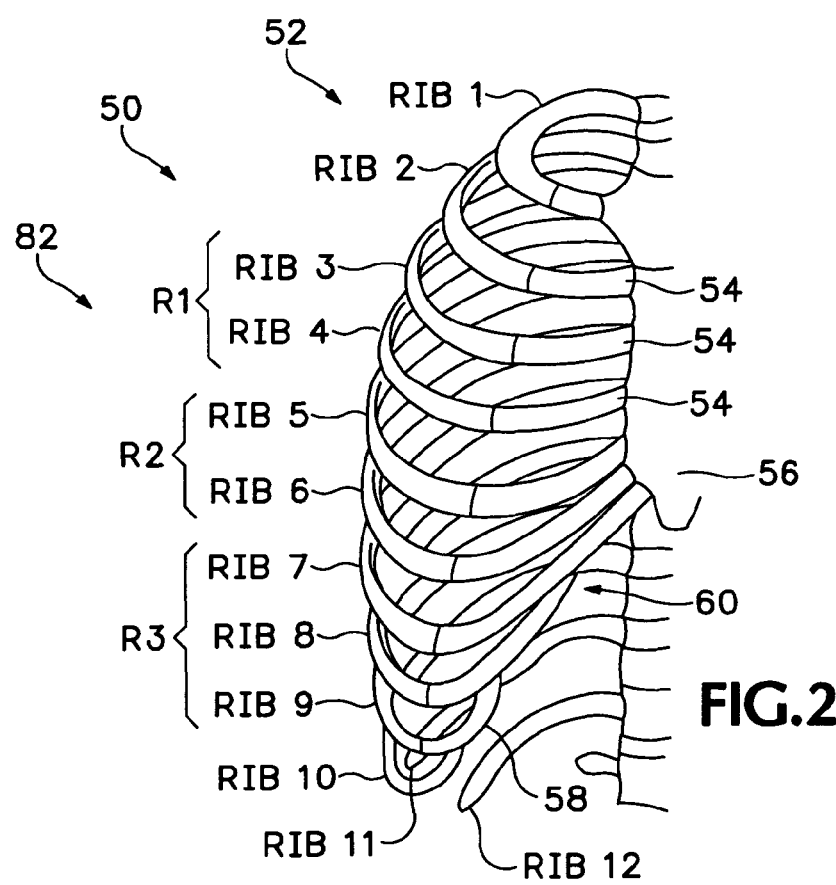
FIG. 2 is an anterior view of the right half of a human rib cage, with individual ribs identified according to anatomical position, and with the ribs assigned to exemplary groups based on similar surface geometries, in accordance with aspects of the present teachings.

FIG. 2 shows an anterior view of the right half of a human rib cage 50. The rib cage includes twelve pairs of ribs (with corresponding right and left ribs for each rib pair). Each rib (or pair of ribs) is identified by a number, shown at 52, according to the anatomical position of the rib within the rib cage. Ribs one through seven, having their own individual cartilaginous connections 54 to the breastbone, or sternum 56, are called true ribs. Ribs eight through ten share a common cartilaginous connection 58 to the sternum, which in turn joins that of the true ribs, shown at 60. Ribs eleven and twelve are not connected to the sternum and are referred to as floating ribs.

Averaged surface geometries of ribs three through nine of the human rib cage were determined from a set of human cadavers. In particular, rib specimens were analyzed after removed from eight fresh-frozen human cadavers (four male, four female). The outer surfaces of these rib specimens were digitally mapped to determine contouring parameters (in-plane longitudinal curvature, twist, and out-of-plane longitudinal curvature). In other exemplary analyses, surface geometries may be measured, for example, from a different subset (or all) of the ribs (e.g., including ribs one, two, ten, eleven, and/or twelve), from living subjects (invasively or non-invasively, such as by MRI), from a different number of subjects, a different representative population, and/or the like.

The unrolled curvature of each rib specimen in the set was measured. Unrolled curvature, as used herein, is a curvature (or bend) in a surface representation of a rib that remains after the surface representation is "unrolled" onto a plane. This unrolling may include removing twist and/or longitudinal curvature(s) from the surface representation. (Similarly, the unrolled curvature of a bone plate is any curvature that remains in the bone plate after the inner surface of the bone plate is unbent/untwisted onto a plane (so that the thickness dimension of the plate is orthogonal to the plane).)

Figure 3:
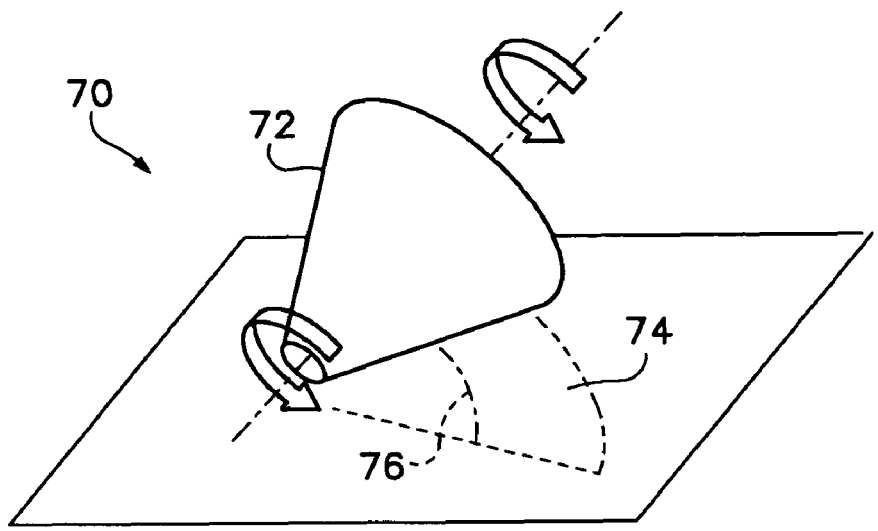
FIG. 3 is a schematic illustration of an exemplary strategy for determining the unrolled curvature (in-plane curvature) of a three-dimensional surface, such as a conical surface or the longitudinal outer surface of a rib, in accordance with aspects of the present teachings.

FIG. 3 shows a strategy 70 for determining the unrolled curvature (in-plane curvature) of a three-dimensional surface, such as a conical surface 72 or the outer surface of a rib. The three-dimensional surface may be unrolled to provide a two-dimensional representation 74 of the surface. An unrolled centerline 76 of the conical surface (or of a rib outer surface) may have a radius of unrolled curvature ($R_u$) that is related reciprocally to the unrolled curvature ($C_u$). (More generally, any curvature is reciprocally related to its radius of curvature.) In some examples, a three-dimensional surface, such as a rib outer surface, may be approximately cylindrical, rather than frustoconical, so that the unrolled curvature of the surface is close to zero.

Figure 4:
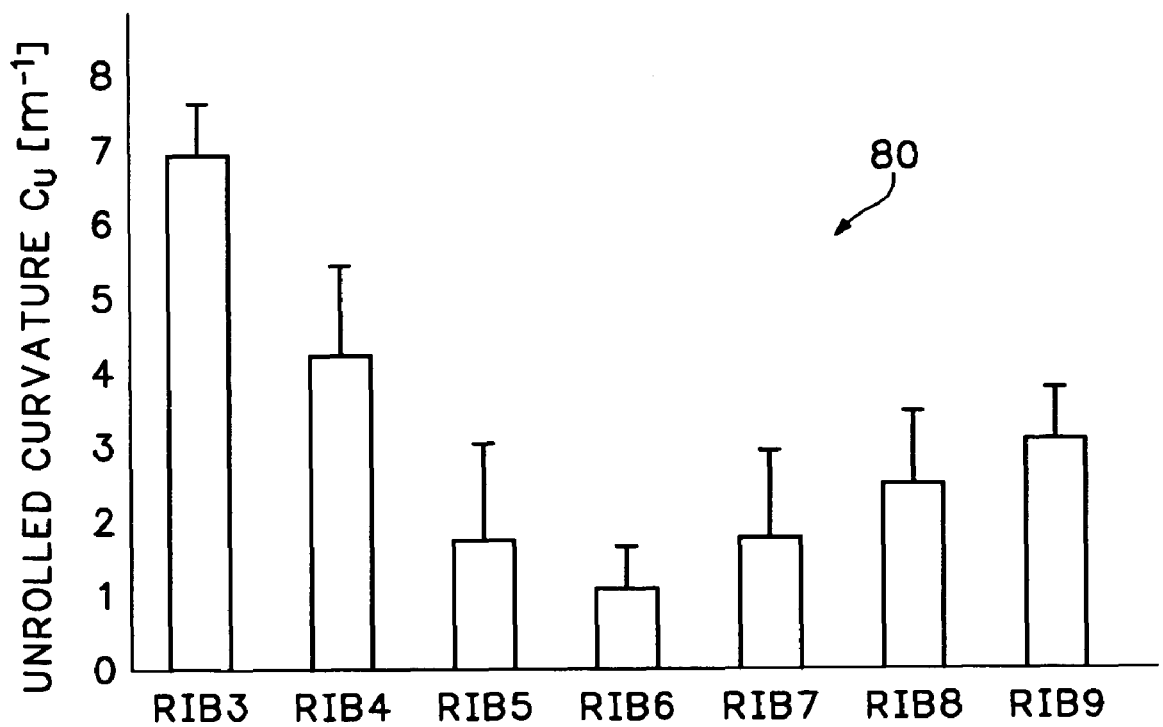
FIG. 4 is a graph of the average unrolled curvature of the longitudinal outer surface of ribs number three through nine, as determined from the ribs of a plurality of human cadavers according to the strategy of FIG. 3, in accordance with aspects of the present teachings.

FIG. 4 shows a graph 80 of the average unrolled curvature ($C_u$) of the outer surface (in particular, the unrolled centerline of this surface) of ribs number three through nine, determined from the rib specimens of the set of human cadavers. The graph shows that the measured curvature $C_u$ of the unrolled centerline changed significantly in magnitude and direction from rib three through rib nine. The curvature $C_u$ was most pronounced in rib three with a magnitude of 7.0 $m^{-1}$. The curvature $C_u$ was smallest in rib six with a magnitude of 1.1 $m^{-1}$. Furthermore, ribs three through five were curved in a direction opposite to ribs six through nine.

The data of FIG. 4 thus shows ribs three through nine each have a unique radius of unrolled curvature $R_U$. Accordingly, a bone plate with a corresponding radius of unrolled curvature may be fabricated for each of these ribs. However, to reduce the number of bone plates fabricated, ribs of similar shape can be grouped (and their surface geometries/curvatures averaged), for example, as shown at 82 in FIG. 2. In particular, right ribs three and four may form group R1, right ribs five and six may form group R2, and right ribs seven through nine may form group R3. The left ribs can be grouped correspondingly into groups L1, L2, and L3. Rib plates configured to be installed on ribs of groups R1 and L1 may have an in-plane longitudinal curvature ($C_U$) of greater than zero, a radius of in-plane longitudinal curvature of about 100-300 mm, or of about 200 mm. Rib plates configured to be installed on ribs of groups R2 and L2 may be substantially straight, for example, with a curvature $C_U$ of about zero. Rib plates configured to be installed on ribs of group three may have an in-plane longitudinal curvature of greater than zero, a radius of in-plane curvature of about 300-500 mm, or of about 400 mm. Rib plates configured for ribs of group one (R1 and L1) and group three (R3 and L3) may be curved longitudinally in opposite directions (in-plane) relative to each other when installed on bone. In particular, rib plates for ribs of group one may be concave, and rib plates for ribs of group three may be convex, when viewed from superior, that is, when installed on appropriate rib bones and viewed from the perspective of a patient's head.

These groupings of ribs presented here are exemplary. In other examples, ribs may be grouped differently (and plate contours selected accordingly) based on the same or different measurements, such as twist and/or out-of-plane longitudinal curvature (see below).

The longitudinal twist of each rib specimen was measured for the set cadaver ribs. In the data presented here, ribs three through nine were found to have a common characteristic twist about their longitudinal axes.

Figure 5:
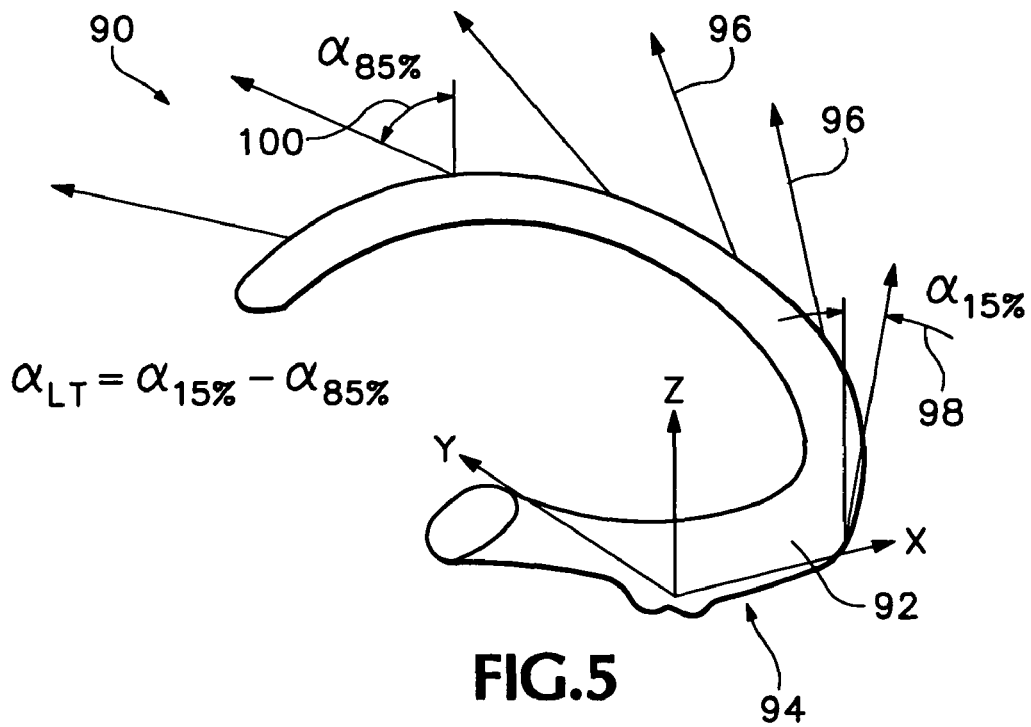
FIG. 5 is an illustration of an exemplary strategy for measuring the twist of the outer surface of a rib bone along the length of the rib bone, based on changes in the orientation angle of the outer surface of the rib bone, in accordance with aspects of the present teachings.

FIG. 5 shows an exemplary strategy 90 for measuring the twist of the outer surface 92 of a rib bone 94 along the length of the rib bone. Twist may calculated by quantifying changes in the orientation angles $\alpha_i$ of the outer cortical surface, shown at 96. In particular, a total longitudinal twist $\alpha_{LT}$ may be defined as the difference between $\alpha_i$ values obtained at 15% and 85% of the rib length (posterior to anterior), indicated at 98 and 100, respectively.

Figure 6:
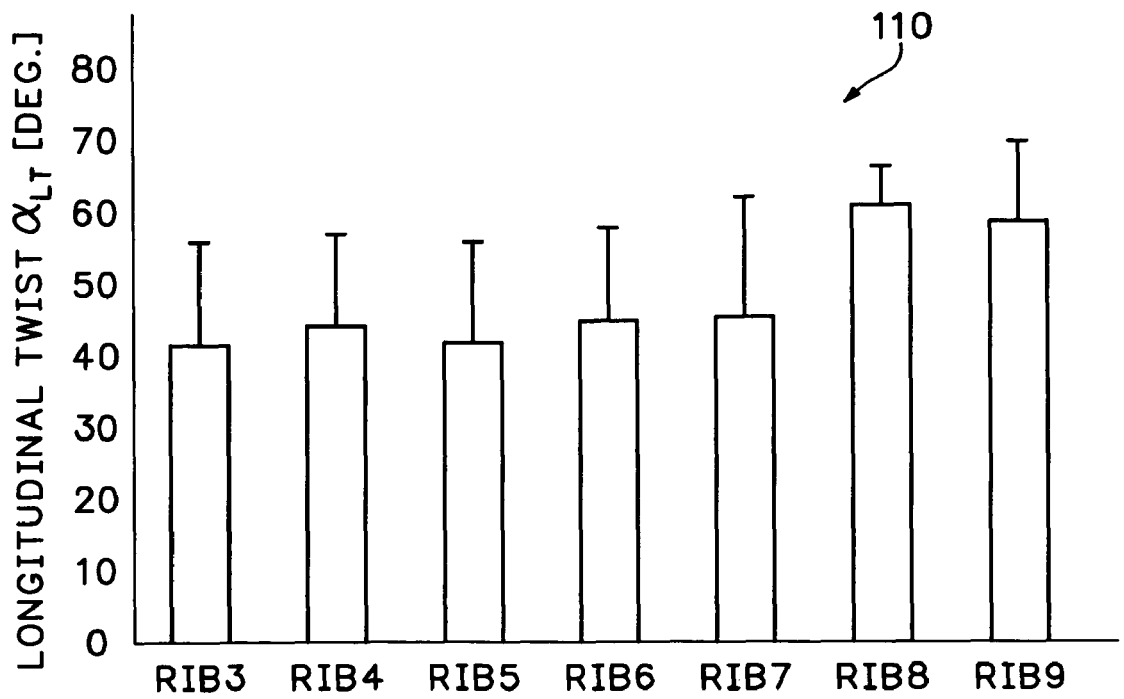
FIG. 6 is a graph of the average longitudinal twist of the outer surface of ribs number three through nine, as determined from the ribs of a plurality of human cadavers according to the strategy of FIG. 5, in accordance with aspects of the present teachings.

FIG. 6 shows a graph 110 of the average total longitudinal twist of the outer surface of ribs number three through nine determined from the rib specimens of the set of human cadavers, according to the strategy of FIG. 5. The total longitudinal twist, $\alpha_{LT}$, was observed to be counterclockwise in the right rib specimens and clockwise in the left rib specimens. The total longitudinal twist was smallest for rib three, at 41°±14°, and largest for rib eight, at 60°±6°. The observed variation in magnitude of the total longitudinal twist between ribs three through nine was not statistically significant ($p>0.05$). Based on these twist measurements, and the measured length of the rib specimens, rib plates may be precontoured to include a twist, for example a twist of about one to four degrees, about two to three degrees, or about 2.5 degrees per centimeter of bone plate length and/or of rib length which the plate is intended to cover. A twist of 2.5 degrees per centimeter corresponds to a 1.44-meter screw pitch. Bone plates configured for different ribs, different groups of ribs (see above), and/or different positions along the length of one or more ribs, thus may have the same twist or different twists. Furthermore, the twist may vary or may be constant along the length of each bone plate.

Figure 7:
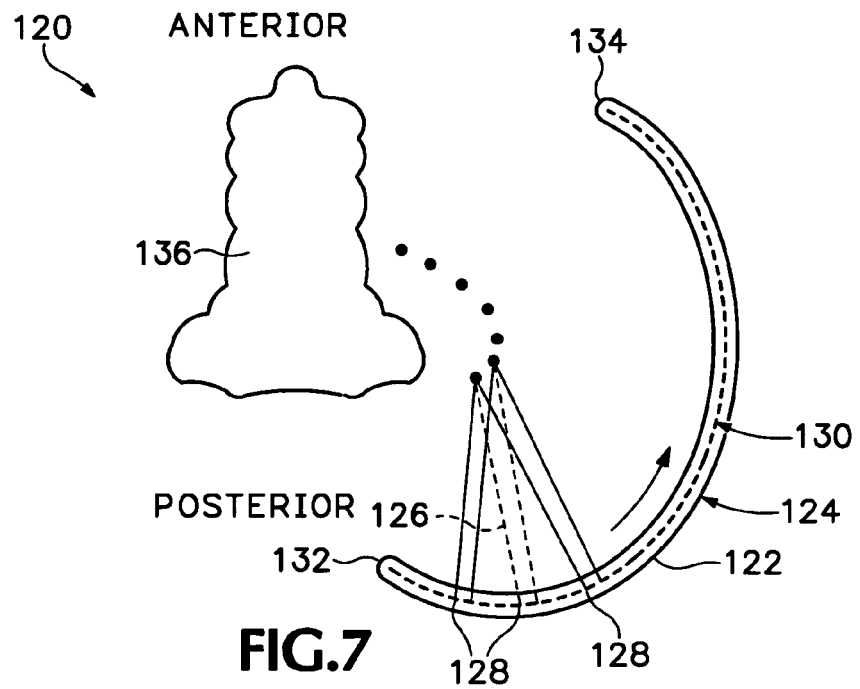
FIG. 7 is an illustration of an exemplary strategy for measuring the out-of-plane longitudinal curvature of an outer rib surface, in accordance with aspects of the present teachings.

The out-of plane longitudinal curvature may be measured from ribs to provide corresponding out-of-plane curvatures for rib plates. FIG. 7 shows an exemplary strategy 120 for measuring the out-of-plane longitudinal curvature of an outer surface 122 of a rib bone 124. In particular, the apparent radius $R_i$ of curvature along the rib, indicated, for example, at 126, may be calculated by fitting circles to point triplets 128 selected from a set of points 130 disposed along the rib. Measurement may be performed at positions along the rib, that is, between the posterior end 132 and the anterior end 134 of the rib, which is more proximate sternum 136. The point triplets may be equally spaced, for example, spaced by about twenty points. In the illustration presented below, custom software code was used to fit circles to a representation of each rib surface.

Figure 8:
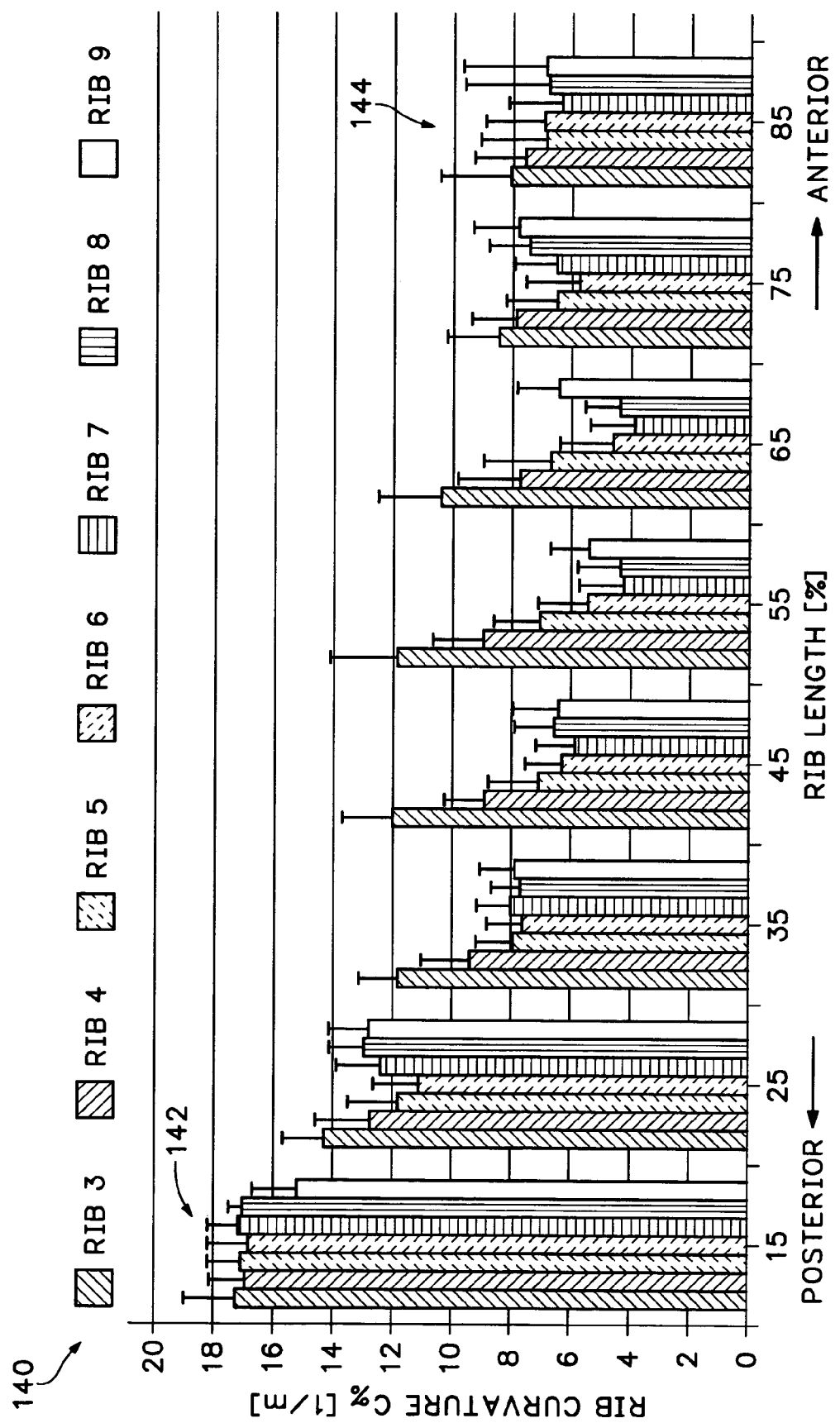
FIG. 8 is a graph of the average out-of-plane longitudinal curvature of the outer surface of ribs number three through nine determined from the ribs of a plurality of human cadavers according to the strategy of FIG. 7, in accordance with aspects of the present teachings.

FIG. 8 shows a graph 140 of the average out-of-plane longitudinal curvature of the outer surface of ribs number three through nine, measured according to the strategy of FIG. 7. The data presented is averaged data for the indicated rib specimens from the set of human cadavers. The apparent radius of out-of-plane longitudinal curvature was expressed as curvature $C\%=1/R_i$ for normalized locations along the rib length. The value of $C_{\%}$ was similar among ribs three through nine at both 15% and 85% rib length, shown at 142 and 144, respectively. In addition, the posterior segment of each rib exhibited more than twice the curvature of the anterior segment. The highest curvature was found in rib three at 15% length with $C_{15}=17.3$ m$^{-1}$. The straightest portion was found in rib seven at 65% length with $C_{65}=3.8$ m$^{-1}$.

Based on the data of FIG. 8, each bone plate may be precontoured to include out-of-plane longitudinal curvature (and/or out-of-plane longitudinal curvature may be introduced intra-operatively). The rib plates corresponding to each group of ribs may be precontoured to include an out-of-plane radius of curvature of at least about 50 mm or 100 mm. In some examples, a subset of the bone plates may have a larger radius of out-of-plane curvature. For example, rib plates for ribs of groups two and three may have a larger radius of out-of-plane longitudinal curvature, such as a radius of curvature of about 125-200 mm or about 150 mm, and rib plates for group one may have a smaller radius of out-of-plane curvature, such as a radius of curvature of about 75-125 mm or about 100 mm. In some examples, the rib plates for different groups of one or more ribs may have the same radius of out-of-plane curvature. Furthermore, in some examples, different rib plates may be configured for different positions along one or more ribs. For examples, a posterior rib plate of greater out-of-plane longitudinal curvature (a smaller radius of curvature) may be configured to be installed on a posterior region of a rib, and an anterior rib plate of lesser out-of-plane longitudinal curvature may be configured to be installed on an anterior region of a rib.

In this example, fourteen different ribs of a rib cage can be fixed with a set of six precontoured bone plates. Thus, the ratio of different ribs to different precontoured rib plates may be greater than two to one. In some examples, the ratio of ribs to rib plates may be one to one, less than one to one, or greater than one to one, among others.

III. Kits for Fixing Rib Bones

The present teachings provide kits for fixing rib bones. The kits may include one or more rib plates, fasteners (such as bone screws) for securing the rib plates to rib bones, a bending tool(s) to adjust the shape of the rib plates, wires (such as K-wires) for guiding bone screws into bone, a drill (and/or drill bits) for forming bores in bone to receive the bone screws, a driver for turning the bone screws, and/or instructions for use of kit components. In some examples, the instructions may correlate rib plates (and/or indicia thereof) with rib bones (or rib regions) for which the rib plates are precontoured. Components of the kits, particularly components used during surgery (such as rib plates, bone screws, drill bits, etc.) may be supplied in a sterile (or nonsterile) condition, for example, packaged in a sterilized container.

Each kit may include a single bone plate or a set of bone plates. The set of bone plates may be configured for use on all or a subset of rib bones of the rib cage. For example, the set may be configured for exclusive use on rib bones on the left side of the rib cage or exclusive use on rib bones on the right side of the rib cage. Alternatively, or in addition, the set may be configured for exclusive use on the anterior regions of rib bones or exclusive use on the posterior regions of rib bones. In some examples, the set may be configured for use on a consecutive subset of the rib bones, such as ribs three through nine (see Section II), among others. Furthermore, the set may be configured for a subset of the general population, such as adults, children, males, females, a particular range of body/frame sizes, etc. In some examples, the set may include rib plates of different length, width, thickness, and/or number/size/shape of holes, among others.

Bone plates within a set may be identifiable by any suitable aspect. For example, the bone plates may be disposed in labeled packages or located adjacent labeled positions within the kit. Alternatively, or in addition, the bone plates may be identifiable using indicia of the bone plates. Indicia, as used herein in reference to bone plates, may include any features of the plates that permit the plates to be distinguishable and identifiable. Exemplary indicia include surface structure (projections, depressions, openings, ridges, grooves, notches, etc.), alphanumeric characters, codes (such as barcodes), and/or colors, among others. Accordingly, each bone plate may have indicia (or an indicium) that identifies the side of the rib cage (left/right) the rib bone (or set of rib bones), and/or the position within a rib for which the plate is precontoured. For example, the bone plate may be marked with the letter "L" for left or the letter "R" for right. Alternatively, or in addition, the bone plate may be marked with a number, such as "3," to indicate that the bone plate is precontoured for use on the third rib bone or for use on a third set of one or more rib bones, among others. In some examples, the bone plates may be distinguishable based on a color of each plate. In some embodiments, indicia may be included in the bone plates to allow a user to determine the intended orientation of the bone plates on bone, for example, to mark a more anterior and/or a more posterior end of each bone plate.

IV. Methods of Making Precontoured Rib Plates

Precontoured rib plates may be fabricated by any suitable methods. Exemplary methods may introduce precontours (that is, pre-operative contours) into a plate member during and/or after creation of the plate member.

Precontours may be introduced during creation of a plate member by any suitable approach. For example, the precontours may be introduced by removing material (by machining) from a larger precursor structure. Alternatively, or in addition, the contours may be introduced by molding the plate.

Contours may be introduced, at least partially, after creation of a plate member by any suitable approach. For example, a parent plate member may be created in a non-precontoured or incompletely precontoured form by any suitable method, such as cutting, machining, stamping, molding, etc. This parent plate member may include in-plane longitudinal curvature or may be substantially linear. In any case, the parent plate member may be shaped by bending and/or twisting to produce a more fully precontoured rib plate.

Rib plates may be formed of any suitable biocompatible materials, particularly biocompatible materials that are malleable. Exemplary malleable biocompatible materials include metal (such as stainless steel, titanium alloy, etc.). In other examples, the rib plate may formed of, or may include, plastic, ceramic, a bioresorbable material (such as a bioresorbable polyester, among others), and/or the like.

V. Methods of Using Precontoured Rib Plates

The precontoured rib plates of the present teachings may be used in methods of fixing rib bones. Exemplary steps of these methods are presented below. These steps may be performed in any suitable order, in any suitable combination, and any suitable number of times.

A rib bone to be fixed may be selected. The rib bone may have a discontinuity and/or may be structurally unsound for another reason. Exemplary discontinuities of the rib bone may include a fracture(s) (e.g., a single fracture, multiple fractures, etc.), a bone nonunion (due to injury, disease, or developmental defect, among others), a malunion, a cut (e.g., produced during an osteotomy), and/or the like. In some examples, the rib bone selected may be multiply fractured and/or may be part of a flail chest injury (see the Background section). Selection of the rib bone may include selection of a surface region of the rib bone onto which a rib plate will be installed.

Segments of the rib bone may be aligned, for example, a fracture(s) reduced. Alignment may be performed non-invasively (e.g., before formation of a soft tissue opening) or invasively, with access through a soft tissue opening. In some examples, alignment of bone segments may be performed, at least partially, by securing a bone plate to the rib bone.

A rib plate for installation may be selected. The rib plate may be selected after the rib bone was selected and based on an aspect of the rib bone selected and/or an aspect of a region to be fixed within the rib bone. The aspect may relate to the anatomical position of the rib bone or rib bone region, for example, its numbered position, left- or right-sided location, and/or anterior-posterior position within the rib cage, among others. In some examples, the rib plate may be selected based on correspondence between an indicium or indicia of the bone plate (and/or indicia of a bone plate label and/or a bone plate holder/organizer). In some examples, the correspondence between rib bones (and/or bone regions) and indicia may be defined by instructions associated with the rib plate. Alternatively, or in addition, selection of a rib plate may include selection of rib plate from a set of rib plates of different length. Selection of the length of a rib plate may be performed, for example, based on the number and/or spacing or fractures in the selected rib bone.

The shape of the rib plate may be adjusted to improve how well the rib plate (and particularly its inner surface) conforms to the bone surface region onto which the rib plate is being installed. Adjusting the shape of the rib plate may be necessary because the rib plate may be precontoured for an averaged surface geometry rather than for the individual geometry of the patient's selected rib bone. Adjusting the shape of the rib plate may be performed by any suitable strategy. For example, the shape may be adjusted with a bending tool(s) (such as pliers, a crimping tool, etc.), a plate holder (such as a vise or clamp), a die, etc.

The rib plate may be secured to the selected rib bone. Generally, the rib plate is secured to the selected rib bone so that the rib plate bridges a fracture or other discontinuity (or discontinuities) of the rib bone. In some examples, the plate may be positioned to bridge two or more fractures of a multiply fractured rib bone. Securing the rib plate to the rib bone may be performed with any suitable fasteners (bone screws, wires, pins, etc.). Exemplary securing may be performed with bone screws placed through holes of the rib plate and into threaded engagement with underlying bone. The bone screws may be placed into pre-formed bores in the rib bone, and/or the bone screws may be self-drilling and/or self-tapping. Furthermore, the screws may extend bi-cortically or uni-cortically in bone. In some examples, one or more of the bone screws may thread into engagement with a threaded hole of the rib plate, thus locking the bone screws to the plate. Further aspects of threaded engagement between bone plates and bone screws are described in U.S. Pat. No. 5,709,686, which is incorporated herein by reference.

Any or all of the steps described above may be repeated to install one or more additional rib plates on the same or different rib bones of the same patient. In some examples, these steps may be repeated to install rib plates, in any order, on a consecutive set of multiply fractured rib bones to treat flail chest injury.

VI. An Exemplary Rib Plate

Figure 9:
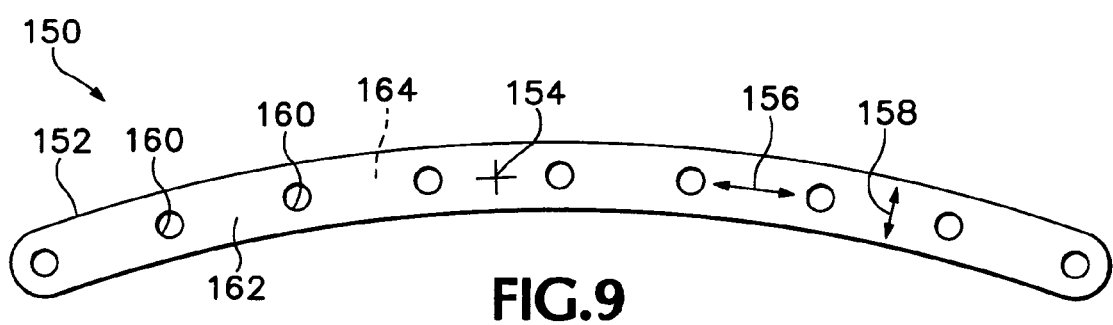
FIG. 9 is a plan view of an exemplary precontoured bone plate for fixing rib bones, showing an in-plane longitudinal curvature of in the bone plate, in accordance with aspects of the present teachings.
Figure 10:
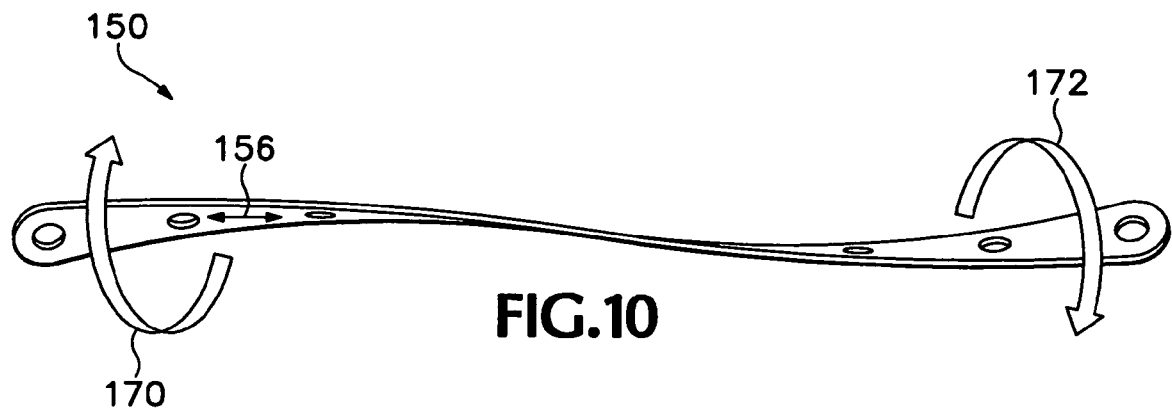
FIG. 10 is a side view of the bone plate of FIG. 9, showing a longitudinal twist introduced in the bone plate, in accordance with aspects of the present teachings.
Figure 11:
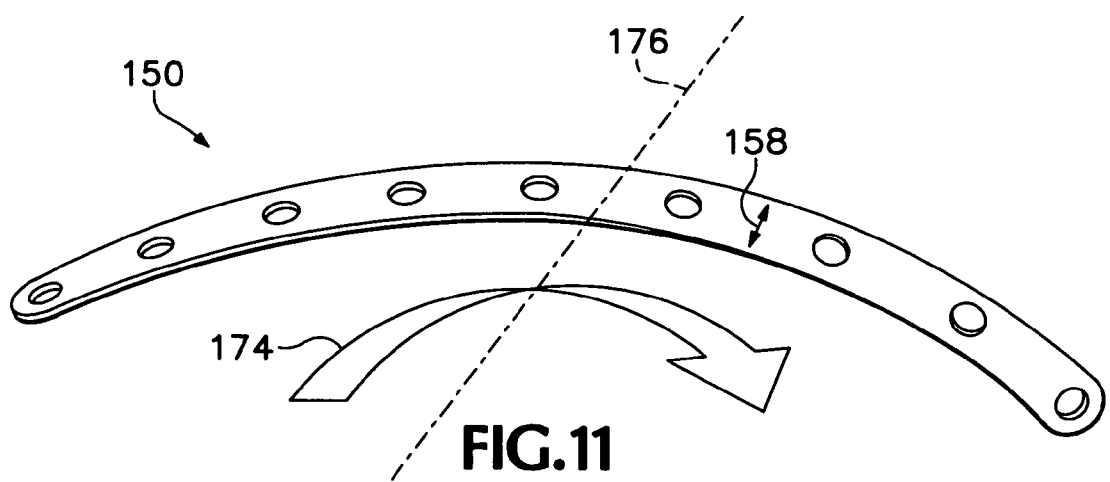
FIG. 11 is a view of the bone plate of FIG. 9, showing an out-of-plane longitudinal curvature introduced in the bone plate, in accordance with aspects of the present teachings.

This section describes an exemplary precontoured bone plate for fixing rib bones, and an exemplary method of constructing the precontoured bone plate; see FIGS. 9-11.

FIG. 9 shows an exemplary precontoured bone plate 150 for fixing rib bones. Bone plate 150 includes a plate member 152 having an in-plane longitudinal curvature about an axis parallel to an orthogonal axis 154 of the plate member. The orthogonal axis may be defined with the plate member in a planar configuration, as shown here, and extends generally orthogonal to a plane defined by the long axis 156 and a transverse axis 158 of the plate member.

Bone plate 150 may define a plurality of openings 160 arranged along the length of the plate member. Openings 160 are generally through-holes extending between outer surface 162 and inner surface 164 of the bone plate. Each opening may be threaded or nonthreaded.

Figure 9A:
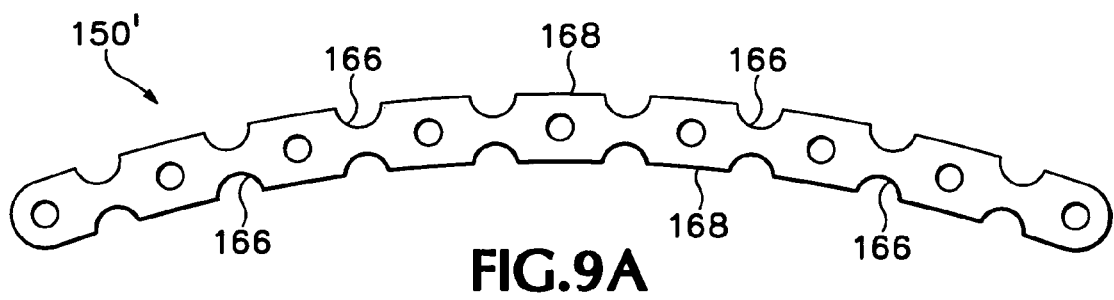
FIG. 9A is a plan view of an alternative embodiment of the bone plate of FIG. 9.

FIG. 9A shows an alternative bone plate 150' including a plurality of lateral notches 166. The lateral notches may be defined by one or both opposing lateral edges 168 of the bone plate. Lateral notches be disposed, for example, at positions intermediate the holes, and may provide sites at which the bone plate bends more readily. Furthermore, the lateral notches may be configured to receive a bending tool, among others.

Bone plate 150 (or plate 150') may be supplied only with an in-plane longitudinal curvature or may include additional precontours. FIG. 10 shows a longitudinal twist introduced into the planar bone plate of FIG. 9. The longitudinal twist may be formed, for example, by urging opposing ends of the bone plate in opposite rotational directions, as shown at 170 and 172. The longitudinal twist thus is formed generally about long axis 156 of the plate. FIG. 11 show an out-of-plane curvature introduced into the twisted bone plate of FIG. 10. The out-of-plane curvature may be introduced, for example, by bending the bone plate, shown at 174 about a bending axis 176 generally parallel to a transverse axis 158 of the bone plate.

VII. Aspects of Precontoured Rib Plates

The present teachings provide precontoured bone plates for fixing ribs. These precontoured bone plates may have any configuration.

The precontoured bone plates may have any suitable length. The length of a precontoured bone plate may be selected according to the length of the bone region to be fixed. For example, a rib bone with a single fracture may be fixed with a shorter bone plate than a multiply fractured rib bone, and a multiply fractured rib bone with closely spaced fractures may be fixed with a shorter bone plate than rib bones having fractures of greater spacing. Exemplary lengths of the bone plates are about 50-300 mm, or about 100-200 mm.

The precontoured bone plates may have any suitable width. For example, a precontoured bone plate may have a width of about 5-15 mm, 8-10 mm, or 9 mm, among others. The width may be substantially constant along the length of the bone plate or may vary, for example, to alter the bendability at one or more narrowed regions of the plate.

The precontoured bone plates may have any suitable thickness. For example, a precontoured bone plate may have a thickness of about 0.5-1.5 mm, or about one millimeter. The thickness may be substantially constant or may vary, for example, so that the plate thins at its perimeter, to decrease the profile of the bone plate on bone.

The precontoured bone plates may have any suitable pre-operative contours. The bone plates may have an in-plane longitudinal curvature or may lack this curvature. An exemplary radius of in-plane longitudinal curvature that may suitable is about ten centimeters to one meter. The in-plane curvature may be distributed uniformly or nonuniformly along the length of each plate, for example, to produce a gentle curvature or a more localized bend, among others. Precontoured bone plates may include or lack other pre-operative contours such as longitudinal twist and/or out-of plane longitudinal curvature. Exemplary longitudinal twist may include about one to four degrees per centimeter of plate length. The handedness of the longitudinal twist may be opposite for plates configured for use on the left side versus the right side of the body. The twist may be constant or may vary along the length of the plates. Precontoured bone plates may bend away from the long axis of the plate and out of the plane of the plate, to produce out-of-plane longitudinal curvature. Out-of-plane curvature, as used herein, is distinct from transverse curvature of the bone plates. In general, transverse curvature is curvature about an axis generally parallel to the long axis of the bone plates, and out-of-plane longitudinal curvature is curvature about an axis nonparallel to the long axis of the bone plates. The bone plates may have any suitable radius of out-of-plane longitudinal curvature, for example, about 50-300 mm. The out-of plane curvature may be constant or may vary along the length of the plates.

The bone plates may include a transverse curvature. The transverse curvature may substantially match the approximately elliptical surface of rib bones.

The bone plates may have any suitable openings. The openings may include one or a plurality of holes extending between the inner and outer surfaces of the bone plates. The holes may be disposed along the centerline of each bone plate or may be off-center. Furthermore, the holes may be spaced equally or non-equally. In some examples, the hole may be spaced by about 5-15 mm, or about 10 mm. Each hole may be threaded or nonthreaded, for threaded or nonthreaded engagement, respectively, with bone screws.

The bone plates may have any suitable mechanical properties. For example, the bone plates may be configured to substantially match the strength of ribs, so that the plates have sufficient fixation strength while avoiding critical stress concentrations due to an exceedingly stiff implant. The mechanical properties of the bone plates, such as fixation strength, yield strength, failure mode, as well as the time required for surgical plate application may be evaluated, for example, on cadaveric rib bones before use in patients.

VIII. Selected Embodiments

This section describes selected embodiments of the present teachings, presented here as a series of indexed paragraphs. 1. A rib plate comprising an elongated plate defining a longitudinal axis (X) along its length, a plurality of holes passing perpendicular trough the upper surface (S) of the plate, arranged along the length of the plate for receiving bone screws, wherein said rib plate has one or more characteristic contours to closely conform to the surface geometry of human ribs.

2. The rib plate of paragraph 1, wherein one characteristic contour of the plane is a curvature (R1) within the plane of the plate surface (S) around an axis perpendicular to X.

3. The rib plate of paragraph 2, wherein the curvature R1 has a radius within a range of 0.1 m to 1 m to conform to a range of rib geometries, whereby R1 may be constant or may vary along X within the described range.

4. The rib plate of paragraph 1, wherein another characteristic contour of the plate in addition to the curvature R1 is a helical twist (a) around the longitudinal axis (X) of the plate.

5. The rib plate of paragraph 4, wherein the twist $\alpha$ is within a range of 2 to 3 degrees per centimeter of plate length along X to conform to a range of rib geometries, whereby the preferred value for a is 2.5 degree per cm.

6. The rib plate of paragraph 1, wherein another characteristic contour of the plate in addition to the curvature R1 or the helical twist $\alpha$ is a curvature R2 out of the plane of the plate surface (S) around an axis perpendicular to X, which will conform the plate to the dominant arch of the human rib.

7. The rib plate of paragraph 6, wherein the curvature R2 has a radius within a range of 5 cm to 25 cm to conform to a range of rib geometries, whereby R2 may be constant or may vary along X within the described range.

8. The rib plate of paragraph 1, wherein the lower surface of the plate has a curved shape to conform to the outer surface of ribs, which are nominally elliptical in cross-section.

9. The rib plate of paragraph 1, wherein the longitudinal edges of the plate have a notch for receiving a manipulation instrument.

10. The rib plate of paragraph 1, wherein the plurality of holes are equally spaced along the length of the plate.

11. The rib plate of paragraph 1, wherein at least one hole is threaded and is configured for seating a bone screw having a threaded head, while the remaining holes are configured for seating with regular bone screws.

12. The rib plate of paragraph 1, wherein said plate is made of malleable material such as stainless steel or titanium, allowing said plate to be manipulated to closely conform to the geometry of the rib.

13. A method for rigidly connecting adjacent segments of a fractured rib using the rib plate of paragraph 1.

14. A method of rigidly connecting adjacent segments of a fracture rib by using a plate which is contoured to the shape of the rib by means of a partial or complete sequence of contouring parameters R1, $\alpha$, and R2.

15. An orthopedic fixation system for rib fractures, characterized in that it comprises a selection of said rib plates, contoured to at least one of the parameters R1, $\alpha$, or R2 to conform to specific rib geometries in a range of patients.

16. An orthopedic fixation system for rib fractures, characterized in that it comprises a selection of said rib plates of varying length to span at least one fracture within a given rib.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

We claim:

1. A rib plate kit, comprising:
    a first elongate rib plate defining a plurality of holes configured to receive fasteners that are designed to secure the first plate to a corresponding rib bone, the first rib plate having a pre-operative contour comprising a population-averaged geometry sized and configured to be installed on the rib bone, wherein the population-averaged geometry of the first rib plate defines a radius of longitudinal curvature between about 75 mm and about 125 mm, and a longitudinal twist between about one degree and about four degrees per centimeter of plate length; and
    a second elongate rib plate defining a plurality of holes configured to receive fasteners that are designed to secure the second plate to a rib bone, the second rib plate having a pre-operative contour comprising a population-averaged geometry sized and configured to be installed on a first plurality of rib bones that does not include the rib bone corresponding to the first rib plate, wherein the population-averaged geometry of the second rib plate defines a radius of longitudinal curvature between about 125 mm and about 200 mm, and a longitudinal twist between about one degree and about four degrees per centimeter of plate length,
    wherein at least part of the population-averaged geometry of each of the first and second plates is averaged over at least two ribs from different people.

2. The rib plate kit of claim 1, further comprising a third elongate rib plate defining a plurality of holes configured to receive fasteners that are designed to secure the third plate to a rib bone, the third rib plate having a pre-operative contour comprising a population-averaged geometry sized and configured to be installed on a second plurality of rib bones that is different from the first plurality of rib bones and does not include the rib bone corresponding to the first rib plate, wherein the population-averaged geometry of the third rib plate defines a radius of longitudinal curvature between about 125 mm and about 200 mm, and a longitudinal twist between about one degree and about four degrees per centimeter of plate length.

3. The rib plate kit of claim 2, wherein the longitudinal curvature of the first, second, and third plates each comprises an out-of-plane longitudinal curvature.

4. The rib plate kit of claim 3, wherein the population-averaged geometry of the first plate further defines an in-plane longitudinal curvature.

5. The rib plate kit of claim 4, wherein the in-plane longitudinal curvature has a radius between about 100 mm and about 300 mm.

6. The rib plate kit of claim 3, wherein the population-averaged geometry of one of the second and third plates further defines an in-plane longitudinal curvature.

7. The rib plate kit of claim 6, wherein the in-plane longitudinal curvature of one of the second and third plates is between about 300 mm and about 500 mm.

8. The rib plate kit of claim 7, wherein the population-averaged geometry of the other of the second and third plates defines substantially no in-plane longitudinal curvature.

9. The rib plate kit of claim 1, wherein the longitudinal curvature of each of the first and second plates is averaged from two or more ribs with different locations in a human rib cage so that the plates are configured to be secured to each of the two or more ribs.

10. The rib plate kit of claim 1, wherein the plates are configured to be secured to either at least one left rib bone or at least one right rib bone, but not both.

11. The rib plate kit of claim 1, wherein at least one of the plurality of holes of each rib plate is threaded.

12. The rib plate kit of claim 1, wherein each of the plates has a shape, wherein the plates are constructed of a malleable material so that the plates can be manipulated pre-operatively to adjust the shape.

13. A kit for fixing rib bones, comprising:
    a first elongate rib bone plate defining a plurality of holes configured to receive rib bone fasteners, the first rib bone plate having a pre-operative contour comprising a population-averaged geometry sized and configured to be installed on a corresponding rib bone, wherein the population-averaged geometry defines an in-plane longitudinal curvature having a radius of between about 100 mm and about 300 mm, an out-of-plane longitudinal curvature having a radius between about 75 mm and 125 mm, and a longitudinal twist between about one degree and about four degrees per centimeter of plate length;
    a second elongate rib bone plate defining a plurality of holes configured to receive rib bone fasteners, the second rib bone plate having a pre-operative contour comprising a population-averaged geometry sized and configured to be installed on a corresponding first plurality of rib bones that does not include the rib bone corresponding to the first rib bone plate, wherein the population-averaged geometry of the second rib bone plate defines an in-plane longitudinal curvature having a radius of between about 300 mm and about 500 mm, an out-of-plane longitudinal curvature having a radius between about 125 mm and 200 mm, and a longitudinal twist between about one degree and about four degrees per centimeter of plate length;

wherein the pre-operative contour of each rib bone plate corresponds to at least two different rib bones with different locations in a rib cage.

14. The kit of claim 13, further comprising instructions for identifying the one or more rib bones to which each of the bone plates correspond.

15. The kit of claim 13, wherein the bone plates include distinct indicia that correspond to the one or more rib bones for which each bone plate is precontoured.

16. The kit of claim 13 wherein each rib plate is configured to be secured to either left rib bones or right rib bones, but not both.

17. The kit of claim 13, further comprising a third elongate rib bone plate defining a plurality of holes configured to receive rib bone fasteners, the third rib bone plate having a pre-operative contour comprising a population-averaged geometry sized and configured to be installed on a second plurality of rib bones that is different than the first plurality of rib bones and does not include the rib bone corresponding to the first rib bone plate, wherein the population-averaged geometry of the third rib bone plate defines an in-plane longitudinal curvature having a radius of between about 300 mm and about 500 mm, an out-of-plane longitudinal curvature having a radius between about 125 mm and 200 mm, and a longitudinal twist between about one degree and about four degrees per centimeter of plate length.

18. A rib plate kit, comprising:
a first elongate rib plate defining a plurality of holes configured to receive fasteners that are designed to secure the first plate to a corresponding rib bone, the first rib plate having a pre-operative contour comprising a population-averaged geometry sized and configured to be installed on the rib bone, wherein the population-averaged geometry of the first rib plate defines a radius of longitudinal curvature between about 75 mm and about 125 mm, and a longitudinal twist between about one degree and about four degrees per centimeter of plate length; and a second elongate rib plate defining a plurality of holes configured to receive fasteners that are designed to secure the second plate to a rib bone, the second rib plate having a pre-operative contour comprising a population-averaged geometry sized and configured to be installed on a first plurality of rib bones that does not include the rib bone corresponding to the first rib plate, wherein the population-averaged geometry of the second rib plate defines a radius of longitudinal curvature between about 125 mm and about 200 mm, and a longitudinal twist between about one degree and about four degrees per centimeter of plate length, wherein the longitudinal curvature of each of the first and second plates is averaged from two or more ribs with different locations in a human rib cage so that the plates are configured to be secured to each of the two or more ribs.

19. The rib plate kit of claim 18, further comprising a third elongate rib plate defining a plurality of holes configured to receive fasteners that are designed to secure the third plate to a rib bone, the third rib plate having a pre-operative contour comprising a population-averaged geometry sized and configured to be installed on a second plurality of rib bones that is different from the first plurality of rib bones and does not include the rib bone corresponding to the first rib plate, wherein the population-averaged geometry of the third rib plate defines a radius of longitudinal curvature between about 125 mm and about 200 mm, and a longitudinal twist between about one degree and about four degrees per centimeter of plate length.

20. The rib plate kit of claim 19, wherein the longitudinal curvature of the first, second, and third plates each comprises an out-of-plane longitudinal curvature.

21. The rib plate kit of claim 20, wherein the population-averaged geometry of the first plate further defines an in-plane longitudinal curvature.

22. The rib plate kit of claim 21, wherein the in-plane longitudinal curvature has a radius between about 100 mm and about 300 mm.

23. The rib plate kit of claim 20, wherein the population-averaged geometry of one of the second and third plates further defines an in-plane longitudinal curvature.

24. The rib plate kit of claim 23, wherein the in-plane longitudinal curvature of one of the second and third plates is between about 300 mm and about 500 mm.

25. The rib plate kit of claim 24, wherein the population-averaged geometry of the other of the second and third plates defines substantially no in-plane longitudinal curvature.

26. The rib plate kit of claim 18, wherein the plates are configured to be secured to either at least one left rib bone or at least one right rib bone, but not both.

27. The rib plate kit of claim 18, wherein at least one of the plurality of holes of each rib plate is threaded.

28. The rib plate kit of claim 18, wherein each of the plates has a shape, wherein the plates are constructed of a malleable material so that the plates can be manipulated pre-operatively to adjust the shape.

* * * * *

UNITED STATES PATENT AND TRADEMARK OFFICE
CERTIFICATE OF CORRECTION

| | | |
|---|---|---|
| PATENT NO. | : 7,785,355 B2 | Page 1 of 1 |
| APPLICATION NO. | : 10/971531 | |
| DATED | : August 31, 2010 | |
| INVENTOR(S) | : Marcus Mohr et al. | |

It is certified that error appears in the above-identified patent and that said Letters Patent is hereby corrected as shown below:

Column 7,
Line 52, delete "$C\%=1/R_i$" and insert -- $C_\%=1/R_i$ --.

Column 12,
Line 34, a new paragraph should begin with "1.".
Line 51, delete "(a)" and insert -- ($\alpha$) --.
Line 55, delete "a" and insert -- $\alpha$ --.

Signed and Sealed this
Eighteenth Day of January, 2011

David J. Kappos
*Director of the United States Patent and Trademark Office*